United States Patent [19]
Kozlowski et al.

[11] Patent Number: 4,920,054
[45] Date of Patent: Apr. 24, 1990

[54] SHUTTLE VECTORS FROM RHODOCOCCUS EQUI

[75] Inventors: Maya Kozlowski, Brampton; Wayne Glasse-Davies, Limehouse, both of Canada

[73] Assignee: Allelix, Inc., Mississauga, Canada

[21] Appl. No.: 889,204

[22] Filed: Jul. 25, 1986

[51] Int. Cl.$^5$ .................. C12N 1/20; C12N 15/00; C12N 7/00
[52] U.S. Cl. .................. 435/252.31; 435/172.3; 435/252.32; 435/252.33; 435/320; 935/29; 935/73; 935/74; 935/84
[58] Field of Search .................. 435/68, 172.3, 253, 435/320; 936/29, 72

[56] References Cited

U.S. PATENT DOCUMENTS

| | | | |
|---|---|---|---|
| 4,489,160 | 12/1984 | Katsumata et al. | 435/253 |
| 4,500,640 | 2/1985 | Katsumata et al. | 435/253 |
| 4,514,502 | 4/1985 | Miwa et al. | 435/253 |

FOREIGN PATENT DOCUMENTS 88166 9/1983 European Pat. Off. .
93611 11/1983 European Pat. Off. .

OTHER PUBLICATIONS

Yoshihama et al., *J. Bacteriol.*, 162:591-7, 1985.
Ozaki et al., *Mol. Gen. Genet.*, 196:175-8, 1984.
Youngman, P. et al., *Science*, 228:285-291, (1985).
Schleif, R. F. et al., *Practical Methods in Molecular Biology*, Springer-Verlag, New York, 1981, pp. 196-197.

Primary Examiner—Thomas D. Mays
Attorney, Agent, or Firm—Saidman, Sterne, Kessler & Goldstein

[57] ABSTRACT

Recombinant DNA plasmids capable of functioning as shuttle vectors in *Rhodococcus equi*, Corynebacterium, *E. coli*, *B. subtilis*, or *S. aureus* are disclosed. The recombinant plasmid contains an origin of replication which is functional in Rhodococcus and at least one of *E. coli*, Corynebacterium, *S. aureus*, and *B. subtilis*. Additionally, the plasmid contains a heritable, selectable marker.

18 Claims, 6 Drawing Sheets

CONSTRUCTION OF pMS2 PLASMID

FIG.5

DETAILS OF THE CONSTRUCTION OF pMS20

FIG. 6

DETAILS OF THE CONSTRUCTION OF pMS21

SHUTTLE VECTORS FROM RHODOCOCCUS EQUI

BACKGROUND OF THE INVENTION

1. Field of the Invention

The present invention is directed to novel composite plasmids for use as cloning vehicles in Coryneforms such as Rhodococcus and Corynebacterium, and also in *E. coli, Bacillus subtilis,* and *Staphylococcus aureus.* The composite plasmids of the present invention are capable of replicating in *Rhodococcus equi* and also capable of replicating in other Coryneforms, *E. coli, Bacillus subtilis* and *Staphylococcus aureus.* In addition the composite plasmids include selectable markers, in one instance genes for resistance to antibiotics, in another instance the lacZ gene. The selectable markers may be employed to assign the marker phenotype to a host microorganism. Further, a novel transposon delivery vehicle is disclosed.

2. Background of Related Information

Coryneforms constitute a broad morphological group of bacteria which are widely distributed in nature. The Coryneform group of bacteria are gram-positive microorganisms having a rod or club-like shape. The group is composed of several different genera, the most widely known of which is the Corynebacteria. The Coryneforms are both agriculturally and industrially important microorganisms. Many species inhabit the soil and cause disease in plants such as alfalfa, bean, beet, corn, tomato, potato, wheat and sugar cane. In addition, certain species of the Coryneforms are used industrially in the production of amino acids and in steroid conversions Other strains of Coryneforms have been found to utilize hydrocarbons, and to synthesize emulsifying agents and antitumor agents.

Recombinant DNA plasmids capable of functioning as shuttle vectors in CorYnebacteria have been described previously. Miwa, K. et al., U.S. Pat. No. 4,514,520, disclose Coryneform shuttle vectors capable of being propagated in Corynebacteria/*E. coli* or Corynebacteria/*B. subtilis.* In addition, these shuttle vectors have the capacity to confer cellular resistance to antibiotics. Miwa, et al. further disclose techniques for plasmid manipulation, transformation, and expression.

Ozaki, A. et al., *Mol. Gen. Genet.* 196:175–178 (1984), disclose the construction of a shuttle vector capable of replication in both *Corynebacterium glutamicum* and *E. coli.* The plasmid conferred cellular resistance to kanamycin, tetracycline, ampicillin, and chloramphenicol.

Yoshihama, M. et al., *J. Bacteriol.* 162:591–597 (1985), disclose a Coryneform shuttle vector capable of replicating in both *Corynebacterium glutamicum* and *Bacillus subtilis.* This reference further discloses a transformation protocol resulting in approximately $10^4$ transformants per ug of plasmid DNA.

European Patent Application 0 088 166 A2 discloses plasmid vectors autonomously replicable in the microorganisms belonging to the genus Corynebacterium or Brevibacterium and having appropriate selectable markers and suitable cloning sites These plasmid vectors are utilized to transform a host microorganism selected from the genus Corynebacterium or Brevibacterium, wherein a DNA fragment containing at least one gene is inserted into a vector DNA, and at least one of both DNAs is foreign to the host microorganism.

Katsumata, R. et al., U.S. Pat. No. 4,500,640, disclose plasmids capable of replicating autonomously in a microorganism belonging to the genus Corynebacterium or Brevibacterium and which carry a gene for resistance to streptomycin and/or spectinomycin. The plasmids are disclosed as useful as cloning vectors. Katsumata, R. et al., U.S. Pat. No. 4,489,160, disclose a plasmid obtained from *Corynebacterium glutamicum* containing multiple restriction endonucleases cleavage sites. The plasmids are disclosed as useful for producing vectors for microorganisms belonging to the genus Corynebacterium.

In spite of the recent advances in vector technology, a need has continued to exist for additional shuttle vectors capable of replication in multiple host microorganisms, these shuttle vectors containing heritable, selectable markers.

SUMMARY OF THE INVENTION

Recognizing the need for the development of shuttle vector systems which would provide the capability of replication of recombinant plasmids in a variety of host microorganisms, the present inventors have developed the recombinant plasmids herein disclosed. These recombinant plasmids comprise (a) a minimum genetic region necessary for controlling the capability of plasmid replication in Rhodococcus, (b) a minimum genetic region necessary for controlling the capability of plasmid replication in at least one of *B. subtilis,* Coryneforms, *E. coli,* and *S. aureus* and (c) at least one heritable, selectable marker.

DESCRIPTION OF THE PREFERRED EMBODIMENTS

Rhodococci are widely distributed in nature and have been frequently isolated from soil, fresh water, and from the gut contents of blood-sucking arthropods, with which they may form a symbiotic association (Cross, T. et al., "The Ecology of Nocardioform Actinomycetes," In: Goodfellow, M et al., *The Biology of Nocardiae,* London, New York, San Francisco Academic Press (1976)). *Rhodococcus equi* is commonly associated with pneumonitis in young foals and with suppurative lymphadenitis in swine (Farrelly, B. T., "*Corynebacterium equi* infection in foals in Ireland,"*Irish Veterinary Journal* 23:231–232 (1969)).

Classical selective isolation methods have depended on the ability of a Rhodococci to use hydrocarbons as sole sources of carbon for energy and growth (Cross, et al., supra) Modification of Sohngen's paraffin baiting method have been used to isolate Rhodococcus strains from soil (Portaels, F., "Isolation and distribution of nocardiae in the Bas-Zaire,) *Annales de la Societe Belge du Medicine Tropicale* 56:73–83 (1976).

Figure 1:
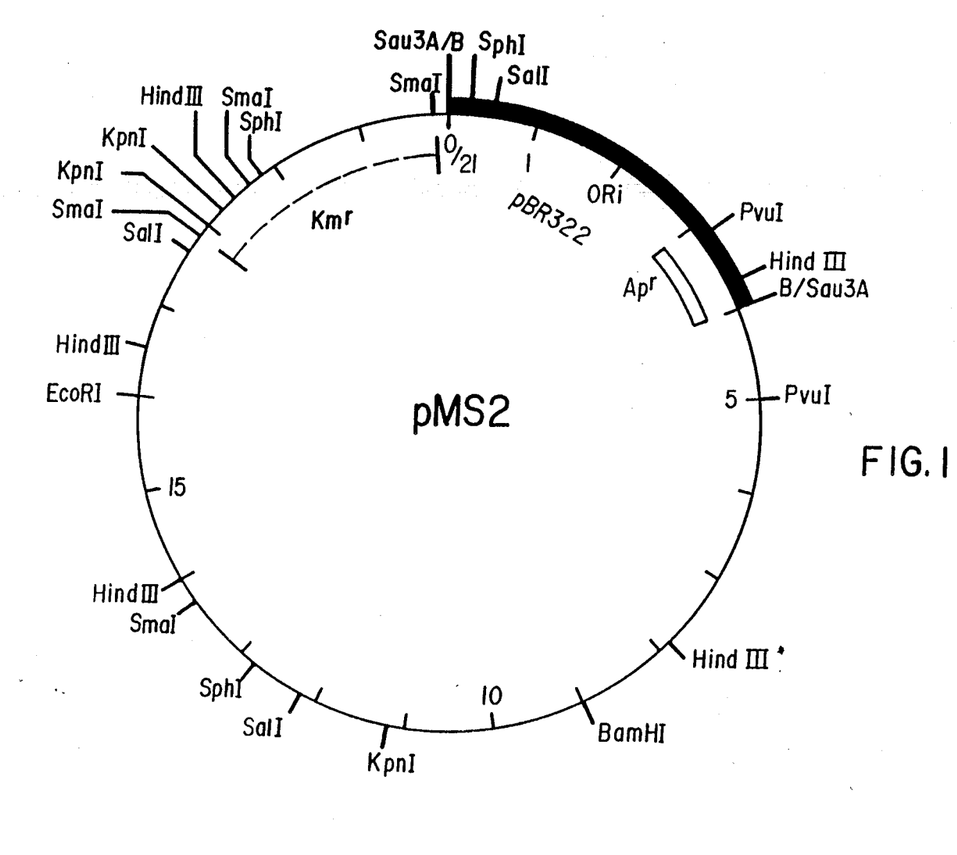
FIG. 1 shows a restriction and functional map of a Rhodococcus/Corynebacterium/*E. coli* shuttle vector, plasmid pMS2.

Two plasmids 5.0 kb and 19.0 kb have been identified in *Rhodococcus equi*. The 19.0 kb plasmid, designated pMS1, was shown to be stably maintained by a plasmid-free Corynebacterium strain ATCC 13059. pMS1 was partially digested with Sau3A enzyme and fused to the BamHI site of pBR322. The resulting shuttle vector, designated pMS2, stably replicates in *E. coli* and Corynebacterium. It specifies ampicillin (Ap) and kanamycin (Km) resistance in *E. coli* and Km resistance in Corynebacterium. At the same time, the fusion plasmid pMS2 contains the origin of replication for Rhodococcus and stably replicates in *Rhodococcus equi* as well. The Km resistance phenotype is of *Rhodococcus equi* origin, and is efficiently expressed in *E. coli* cells. FIG. 1 shows a restriction and functional map of pMS2.

Figure 2:
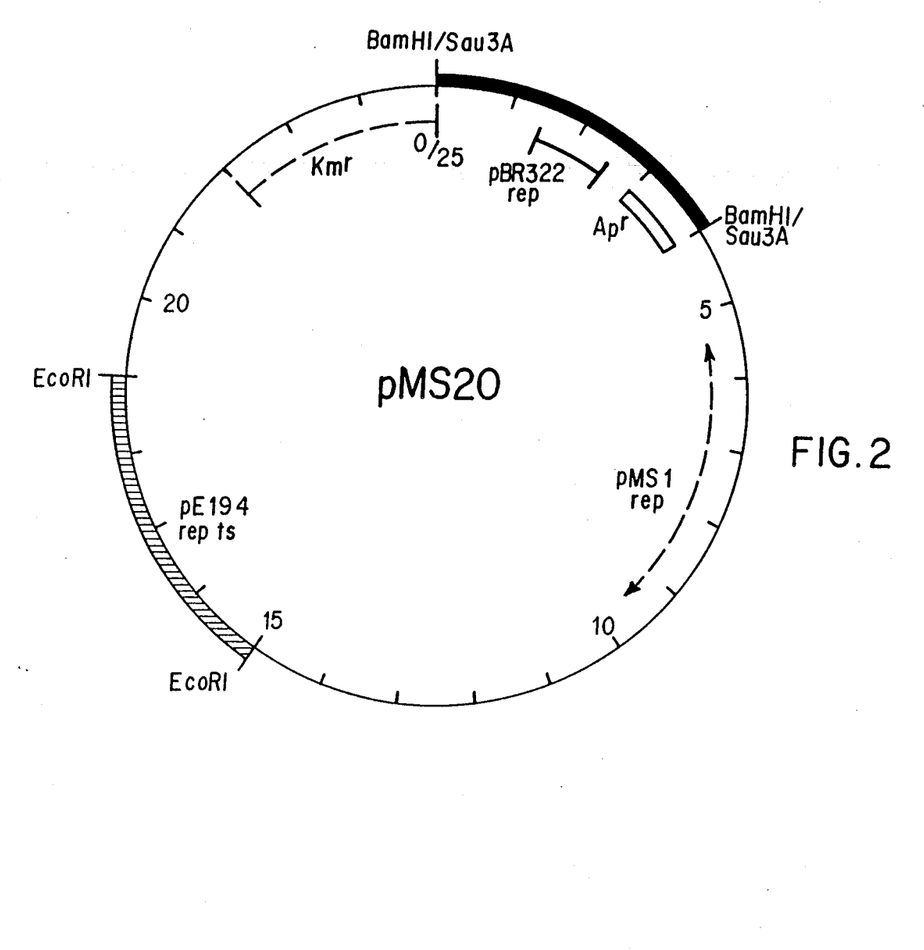
FIG. 2 shows a restriction map of plasmid pMS20, a shuttle vector capable of replication in *S. aureus, B. subtilis, E. coli, R. equi,* and Corynebacterium.

A 4.0 kb EcoRI fragment containing a replication region from *S. aureus* and *B. subtilis*, plasmid pE194, was cloned into EcoRI cut pMS2. The resulting plasmid was designated pMS20. A restriction map of pMS20 is shown at FIG. 2. pMS20 can replicate in *S. aureus, B. subtilis, E. coli, R. equi,* and Cornyebacterium. pMS20 confers ampicillin and kanamycin resistance in *E. coli* and kanamycin resistance in Corynebacterium.

Figure 3:
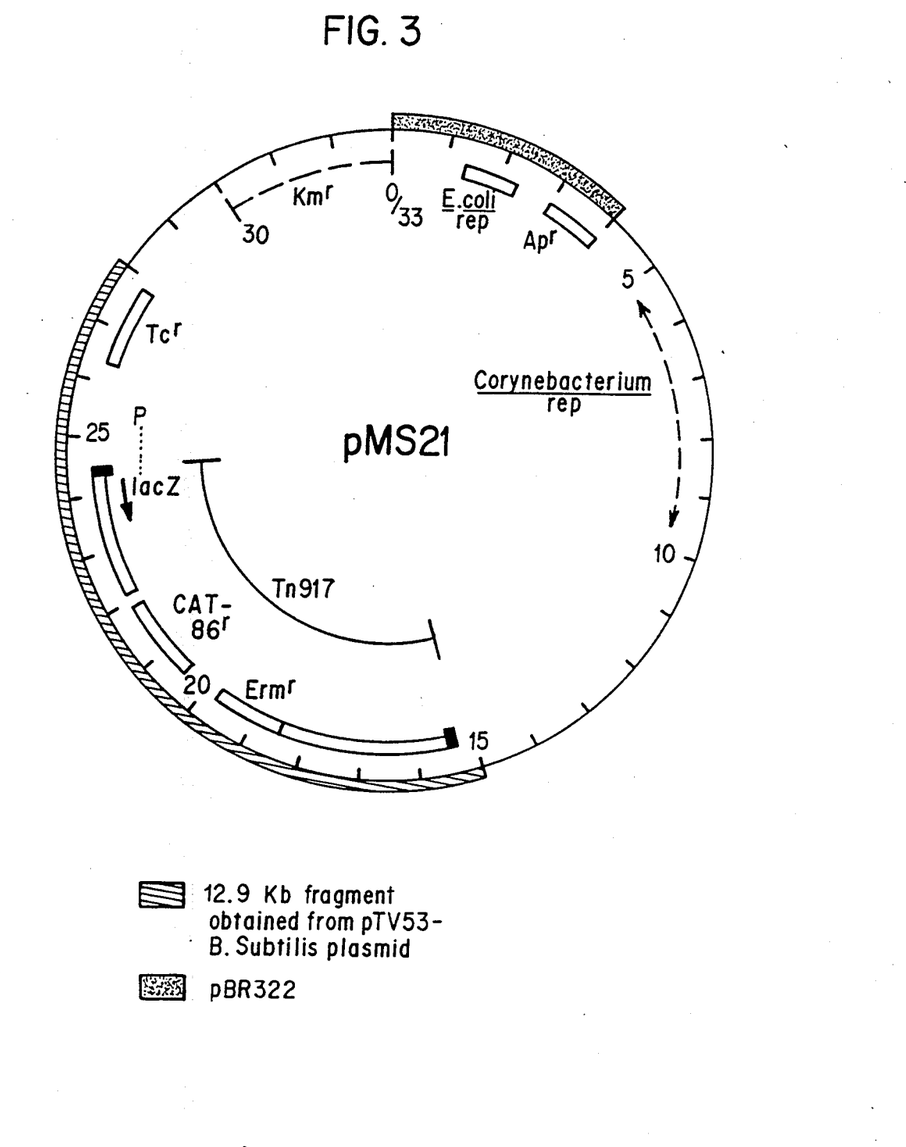
FIG. 3 shows a restriction map of plasmid pMS21. Plasmid pMS21 is a shuttle vector capable of replication in *E. coli,* Corynebacterium, and Rhodococcus. In addition to antibiotic resistances, pMS21 also contains the gene for lacZ expression.

The restriction map of pMS21 is shown at FIG. 3. pMS21 was constructed by cloning a 12.5 kb EcoRI fragment derived from *B. subtilis* plasmid pTV543 to the EcoRI site of pMS2. 12.5 kb ECORI fragment contains tetracycline gene as well as a transposable element Tn917. Tn917 in addition to transposition functions specifies resistance to erythromycin and chloramphenicol.

pMS21 also contains the gene for the lacZ operon which is within the Tn917 element. The resulting *E. coli*/Corynebacterium shuttle plasmid is a promotor probe vector wherein DNA fragments derive from Corynebacterium may be cloned and marked by the expression of the lacZ gene, as well as a transposon delivery vehicle. As may be seen from FIG. 3, pMS21 contains the gene(s) for the transposable element Tn917.

Techniques and detailed steps for the isolation and fusion of shuttle vectors according to the present invention are as follows:

A. Plasmid Isolation from Rhodococcus equi and Corynebacterium ATCC 13059

1. Grow overnight cultures in 1L of yeast-triptone medium (2yt) at 30° C. for about 48 hours.
2. Spin the cells down and resuspend in 45 ml of 10 mM Tris, pH 8.0.
3. Spin the cells again at 5,000 rpm for 15 minutes.
4. Remove supernatant and freeze the pellet for about 1 hour at about −70° C.
5. Thaw the cells at room temperature and resuspend in total volume of about 50 ml ST buffer [ST=0.5 M sucrose, 100 mH Tris pH 8.0]
6. Add about 10 ml of lysozyme [10 mg/ml] made in ST buffer.
7. Incubate the mixture for about 1 hour at about 37° C.
8. To 60 ml suspension add:
   12 ml 5 M NaCl
   3 ml 0.5 M EDTA
   60 ml 2% SDS-0.78 M NaCl.
9. Clear the cell debris and the chromosomal DNA by spinning at about 5,000 rpm for about 1 hour. 10. Transfer the supernatant to a new tube, add PEG to 10% and leave overnight at about 4° C. 11. Spin down at 5,000 rpm for about 15 min, save the pellet. 12. Resuspend the pellet in 7.0 ml of TE buffer. Add about 8 gms of CsCl and 1 ml of Et/Br (10 mg/ml). 13. Place the sample in an ultra centrifuge and run overnight at about 60,000 rpm, 15° C.

B. Transformation of Corynebacterium with Plasmid DNA

1. Grow the cells 16–18 hours at 37° C. in 2YT+2% glucose+2% glycine (20 ml in 250 ml flask).
2. Before starting experiment - plate out original culture on 2YT and sorbitol medium (SB).
3. Spin the cells down at about 7,000 rpm for about 10 min
4. Wash with 1 M sorbitol, about 5 ml, spin at about 7,000 rpm for 10 min.
5. Resuspend in 1 ml of sorbitol-lysozyme (lys: [2.5 mg/ml]).
6. Incubate at about 37° C. for about 90 min without shaking.
7. Spin 7,000 rpm, 10 min - resuspend the cells in 1 ml sorbitol and plate out (protoplasts) on 2YT, and SB media.
8. Transfer 0.3 ml of protoplasts into a 10 ml test tube and add:
   1. DNA, incubate 10 min at RT;
   2. Add 10% glucose - 1.5 ml, mix gently;
   3. Add 0.7 ml of 50% PEG made in 0.5 M sorbitol, mix gently;
   4. Dilute 4 x adding 4 ml of SB medium.
9. Plate out the cells (regeneration) on SB media supplemented antibiotics and overlayed with soft agar containing antibiotics.
10. Incubate at 30° C. for 2-5 days, (transformants should appear after 2 days).

C. Colony Hybridization Modified for Corynebacterium

1. Store a plate containing the colonies at 4° C. prior to use.
2. Place a colony screen disc onto the agar plate (NEN-colony hybridization "Colony screen" filters).
3. Allow the disc to sit on agar plate to adhere for 10 min. (Mark the orientation of the disc).
4. Lift the filter and place it in a Petri dish containing 1 ml of TE-10 mg/ml lysozyme solution.
5. Soak the filter for 1 hr. at 37° C.
6. Dry the filter on Whatman paper.
7. Denature the DNA in 1 M NaOH 1% SDS for about 20 min at room temperature (RT).
8. Wash in 5 M NaCl 1 M Tris-HCl pH 7.5.
9. Dry the filter at RT and use it for hybridization.

D. Rapid, Small Scale Preparation of Plasmid DNA from Corynebacterium

1. Spin down 5 ml of overnight culture of bacteria.
2. Remove the medium by aspiration, leaving the bacterial pellet as dry as possible
3. Freeze the pellet at −80° C. for 30 min.
4. Resuspend the pellet in 100 ml of buffer (50 mM glucose, 10 mM EDTA, 25 mM Tris-Cl pH 8.0).
   Add powdered lysozyme (10 mg/ml) to the solution just before use.
5. Incubate for 15 min at 37° C. or until the solution becomes viscous.

6. Add 200 ul of a freshly prepared solution of 0.24 NaOH, 1% SDS.

7. Store on ice for 5-10 min.

8. Add 150 ml of ice-cold solution of potassium acetate (pH 4.8) store on ice for 10 min.

9. Centrifuge for 5 min in an Eppendorf centrifuge at 4° C.

10. Transfer the supernatant to a fresh tube.

11. Add an equal volume of phenol/chloroform. Mix by vortexing centrifuge for 2 min, transfer the supernatant to a new tube.

12. Add two volumes of 95% Et-OH, spin the pellet down (15 min in an Eppendorf Centrifuge).

13. Wash the pellet with 70% Et-OH, spin down, dry in vacuo.

14. Take up DNA in 30 ul of TE with RNase (20 ug/ml).

Plasmids according to the present invention are useful as these plasmids replicate autonomously in microorganisms belonging to the genus Rhodococcus, and, additionally in one or more microorganisms selected from the group consisting of Bacillus, E. coli, Corynebacteria, and Staphylococcus.

The plasmids of the present invention are fusion products of a first plasmid comprising a minimum genetic region necessary for controlling the capability of plasmid replication in Rhodococcus and a second plasmid comprising a minimum genetic region necessary for controlling the capability of plasmid replication in at least one of B. subtilis, Corynebacterium, E. coli, and S. aureus. In addition, the composite plasmid contains a heritable, selectable marker.

Among the plasmids comprising a minimum genetic region necessary for controlling the capability of replication in Rhodococcus are pMS1, pMS2, pMS20, and pMS21. Plasmid pMS2, contained in an E. coli host, is on deposit at the American Type Culture Collection (ATCC), Rockville, Maryland, under accession No. ATCC 67189.

Plasmids comprising a minimum genetic region necessary for controlling the capability of plasmid replication in E. coli are preferably multi-copy plasmids and have genetic information of resistance to a drug. They include, for example, pAC105, RSF2124, pCR1, pMB9, pBR313, pBR322, pBR324, pBR325, pBR327, pBR328, pKY2289, pKY2700, pKN80, pKC7, pKB158, pMK2004, pACYC177, pACYC184.

Plasmids comprising a minimum genetic region necessary for controlling the capability of plasmid replication in Bacillus subtilis and having genetic information of resistance to a drug are preferably multi-copy, such as, for example, pT127, pCl94, pC221, pC223, pUB112, pUB110, pSA0501, pSA2100, pE194, pTP4, pTP5.

A plasmid of particular utility containing a DNA fragment derived from Bacillus subtilis is plasmid pTV53, said plasmid carrying erythromycin (Er) and chloramphenicol (Cm) resistance.

In order to construct a composite plasmid of the present invention from the precursor first and second plasmids, conventional methods may be employed. For example, both plasmids may be digested by one or several restriction enzymes which form complementary termini, or flush end termini at the cleaved point, and thereafter the disgested plasmids may be ligated with a ligase.

The composite plasmid may also be prepared by cutting both first and second plasmids with one or several restriction enzymes or with shearing force, treating with an exonuclease when required, elongating to complementary single chain oglionucleotides with terminal transferase at the termini of the cut plasmids, and finally, annealing the derivatives of the cut plasmids.

In addition to a minimum genetic region necessary for controlling capability of gene propagation in Rhodococcus and a minimum genetic region necessary for controlling the capability of gene propagation in at least one of Corynebacterium, E. coli, B. subtilis, and S. aureus, the composite plasmid contains as well a heritable, selectable marker. Included among the markers of the plasmids of the present invention are resistance to antibiotics such as kanamycin, chloramphenicol, erythromycin, tetracycline, and ampicillin. Another marker suitable for the practice of the present invention comprises the lacZ operon.

Inasmuch as the composite plasmids produced by the practice of the present invention confer drug resistance, bacteria which contain the composite plasmid may easily be identified by testing for resistance to the drug. Further, because the recombinant plasmid contains an origin of replication for Rhodococcus and at least one of E. coli, S. aureus, B. subtilis, and Corynebacteria, the composite plasmid carrying a foreign gene insertion may be amplified or cloned using Rhodococcus and at least one of E. coli, B. subtilis, S. aureus, and Corynebacterium. For example, pMS2 stably replicates an E. coli, Corynebacterium, and Rhodococcus, specifying Ap and Km resistance in E. coli and Km resistance in Corynebacterium. pMS20 stably replicates in S. aureus, B. subtilis, E. coli, R. equi, and Corynebacterium. pMS21 will stably replicate in Rhodococcus, Corynebacterium, and E. coli.

The fused plasmids may be incorporated into an appropriate host utilizing any of the techniques conventional and well known in the art. Typically, one may utilize calcium chloride to increase the permeability to DNA (Mandell, M. et al., J. Mol. Biol. 53:159 (1970)) or by incorporation at a specific stage of growth when cells become capable of incorporating DNA (competent cells) as disclosed by Duncan, C.H. et al., Gene. 1:153 (1977).

Furthermore the plasmids can be designed by placing appropriate restriction sites thereon, for incorporation of foreign genes into host organisms. Thus the plasmids of the invention can be used as precursors to expression vehicles for production of foreign gene products in a variety of hosts.

Having now generally described this invention, the same will become better understood by reference to certain specific examples which are included herein for purposes of illustration only and are not intented to be limiting unless otherwise specified.

EXAMPLE 1

Construction of pMS2

0.5 ug of pMS1 DNA was partially digested with 0.1 units of Sau 3A enzyme. The reaction was conducted at 37° C. for 4 min. The enzyme was then heat inactivated at 65° for 10 min. 0.2 ug of partially digested pMS1 was used for cloning to BamHI cut pBR322 (0.1 ug). The fragment and vector DNA were mixed in 66 mM Tris (pH7.5), 10 mM MgCl$_2$, 1 mM ATP, 15 mM dithiothreitol, 0.05% BSA and 20 units/uL T4 DNA lipase (new England Biolabs). The reaction was carried out overnight at 15° C.

Figure 4:
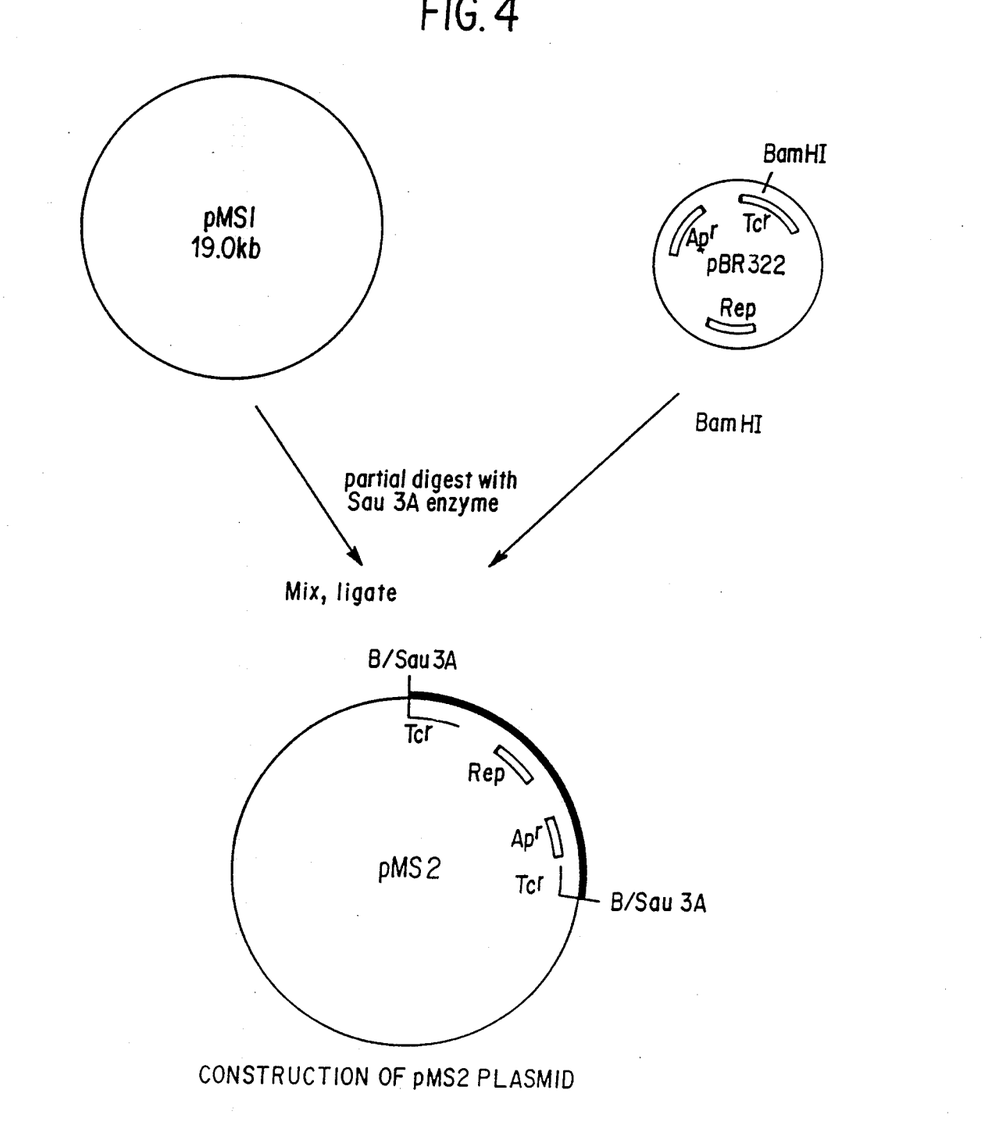
FIG. 4 is a flow sheet for constructing pMS2.

*E. coli* strain RR1 (leu⁻, thi⁻, pro⁻, str', lac⁻, rk⁻, mk⁻) was transformed with the ligation mixture. The transformation and preparation of competent cells were carried out according to Maniatis et al., 1982; Molecular Cloning, laboratory manual, p250. Transformants were select on 2YT agar supplemented with ampicillin (30 ul/ml), and screened for tetracycline sensitivity. Insertion of DNA fragments to the BamHI site of pBR322 inactivates Tc-resistance. Two Tc-sensitive colonies were obtained. Plasmid DNA was purified from both of them and analyzed with restriction enzymes ("minipreps" were done according to Maniatis et al., Molecular Cloning. (A laboratory Manual) 1982, p 368–369). Both colonies contained plasmids which were cointegrates of pMS2 and pBR322. One of the two isolates was designated as pMS2 and used for further studies. FIG. 1 illustrates the restriction and functional map of pMS2 and FIG. 4 shows the steps involved in its construction.

EXAMPLE II

Construction of pMS20

Figure 5:
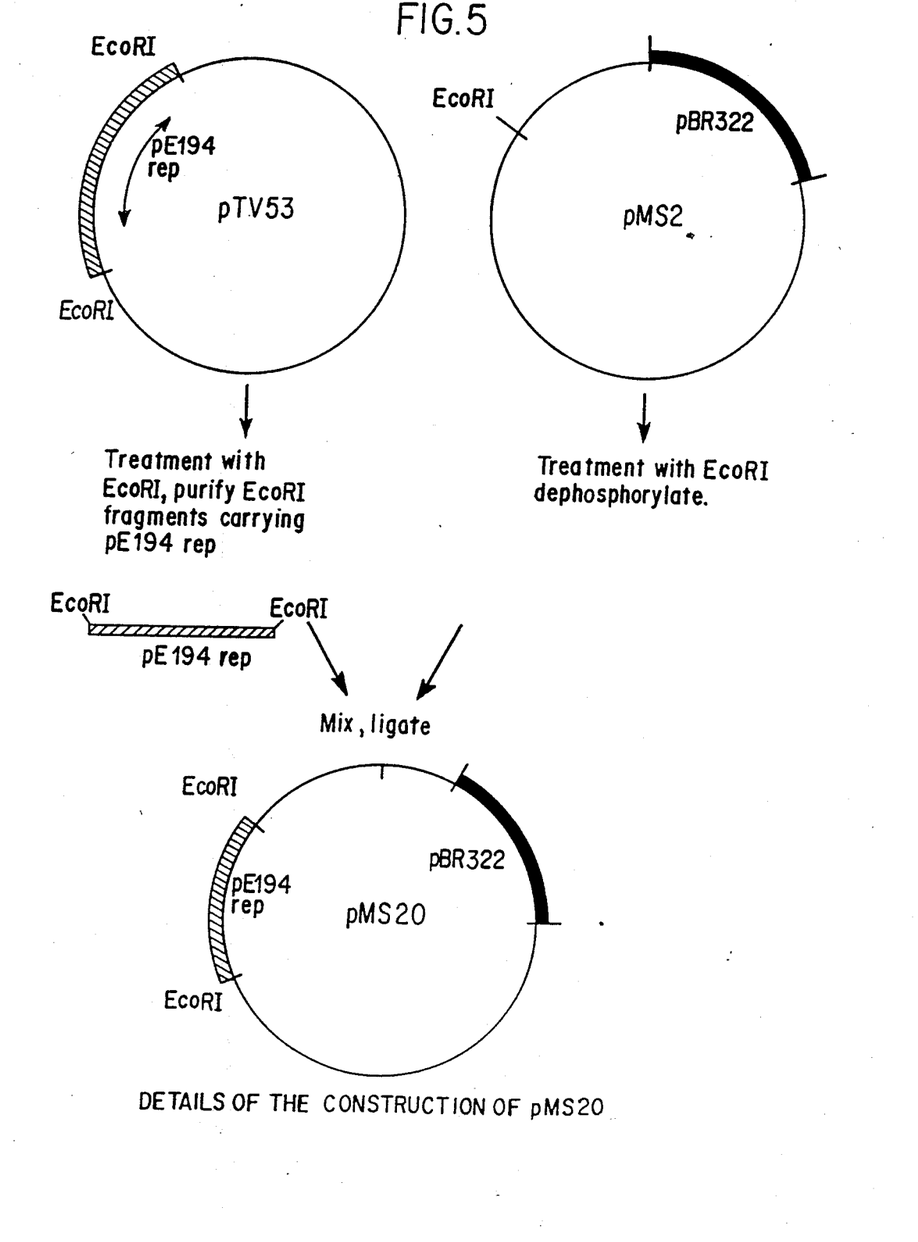
FIG. 5 is a flow sheet for construction of pMS20.

In order to extend the host range of pMS2 a DNA fragment containing the replication region functioning in *S. aureus* and *B. subtilis* was cloned into pMS2. *B. subtilis/S. aureus* rep region was isolated from pTV53 plasmid (Youngman et al., 1985, Science 228:286–291). 10 ug of pTV53 was digested to completion with EcoRI enzyme. 4kb EcoRI fragment carrying the rep. region was purified from the low melting temperature agarose, phenol extracted and ethanol precipitated (all procedures conducted according to Maniatis et al., 1982, p. 170.) 4.0kb EcoRI fragment was cloned into EcoRI cut and dephosphorylated pMS2. 5-molar excess of fragment DNA was adopted. The cloning reaction and the transformation procedure was as described for pMS2 construction. Details of the steps in the construction are illustrated in FIG. 5.

EXAMPLE III

Figure 6:
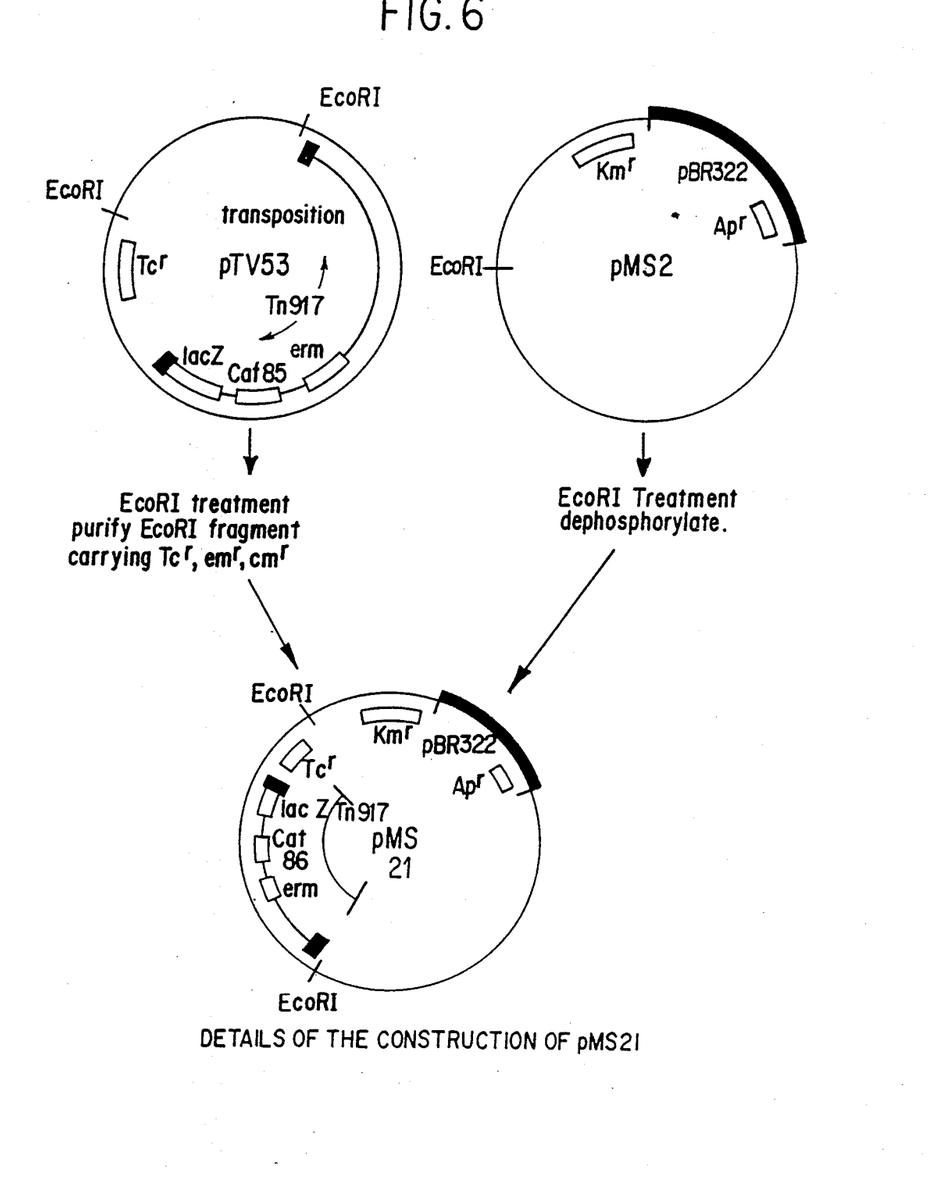
FIG. 6 is a flow sheet for construction of pMS21.

Construction of the Promoter Probe Vector and Introduction of Additional Antibiotic Resistance Genes of Tn917 into pMS2 pMS2 confers only km' in *Rhodococcus equi* and Corynebacteria. It is therefore desirable to introduce additional antibiotic resistance genes to it.

pTV53 plasmid was digested to completion with EcoRI 12.0 kb fragment carrying tet cat86, erm as well as promoterless lacZ gene and the transposition gene(s) of Tn917 was purified and used for cloning to EcoRI cut and dephosphorylated pMS2 (all procedures used were as outlined for the construction of pMS20). The resulting plasmid pMS2 plus EcoRI fragment of pTV53 was designated as pMS21 The steps involved in its construction are illustrated in FIG. 6.

Having now fully described this invention, it will be understood by those with skill in the art that the same may be performed within a wide and equivalent range of conditions, parameters, and the like, without affecting the spirit or scope of the invention or of any embodiment thereof.

What is claimed is:

1. A plasmid which comprises:
    (a) a first minimal genetic region encoding an origin of plasmid replication functional in Rhodococcus; and
    (b) a second minimal genetic region, encoding an origin of plasmid replication functional in at least one selected from the group consisting of *E. coli, Bacillus subtilis,* Corynebacterium, and *Staphylococcus aureus.*

2. The plasmid of claim 1 which is plasmid vector pMS2 having ATCC accession No. 67189.

3. The plasmid of claim 1 which is plasmid vector pMS20.

4. The plasmid of claim 1 which is plasmid vector pMS21.

5. The plasmid of claim 1 wherein said second minimal genetic region is derived from a plasmid selected from the group consisting of pAC105, RSF2124, pCR1, pMB1, pBR313, pBR322, pBR324, pBR325, pBR327, pBR328, pKY2289, pKY2700, pKN80, pKC7, pKB158, pMK2004, pACYC177, pACYC184, pT127, pC194, pC221, pC223, pUB112, pUB110, pSA0501, pSA2100, pE194, pTP4, pTP5, and pTV53.

6. The plasmid of claim 1 wherein said first minimal genetic region is derived from a plasmid selected from the group consisting of pMS2, pMS20 and pMS21.

7. The plasmid of claim 1, further comprising a transposable element.

8. The plasmid of claim 10 wherein said transposable element is Tn917.

9. The plasmid of claim 1, further comprising a gene insert foreign to the transformed host.

10. The plasmid of claim 1 further comprising heritable, selectable markers capable of specifying:
    (a) kanamycin resistance in Corynebacterium and Rhodococcus;
    (b) ampicillin resistance in *Escherichia coli;* and
    (c) kanamycin resistance in *Escherichia coli.*

11. A host transformed with a plasmid wherein said plasmid comprises:
    (a) a first minimal genetic region, encoding an origin of plasmid replication functional in Rhodococcus; and
    (b) a second minimal genetic region, encoding an original of plasmid replication functional in at least one selected from the group consisting of *E. coli, Bacillus subtilis,* Corynebacterium, and *Staphylococcus aureus.*

12. The host of claim 11 wherein said plasmid further comprises heritable, selectable markers capable of specifying:
    (a) kanamycin resistance in Corynebacterium and Rhodococcus;
    (b) ampicillin resistance in *Escherichia coli;* and
    (c) kanamycin resistance in *Escherichia coli.*

13. The host of claim 11 wherein said plasmid is plasmid vector pMS2 having ATCC accession No. 67189.

14. The host of claim 11 wherein said plasmid is plasmid vector pMS20.

15. The host of claim 11 wherein said plasmid is plasmid vector pMS21.

16. The host of claim 11 wherein said plasmid further comprises a transposable element.

17. The host of claim 11 wherein said plasmid further comprises a gene insert foreign to the transformed host.

18. The host of claim 11 wherein said host is selected from the group consisting of Rhodococcus, *E. coli, B. subtilis, S aureus,* and Corynebacterium.

* * * * *

UNITED STATES PATENT AND TRADEMARK OFFICE
CERTIFICATE OF CORRECTION

PATENT NO.  : 4,920,054

DATED       : April 24, 1990

INVENTOR(S) : Maya Kozlowski and Wayne Glasse-Davies

It is certified that error appears in the above-identified patent and that said Letters Patent is hereby corrected as shown below:

On the title page, item [73], the name of the assignee "Allelix, Inc." should be deleted, and the new name of the assignee --Allelix Biopharmaceuticals Inc.-- should be substituted therefor.

Signed and Sealed this

Third Day of March, 1992

Attest:

HARRY F. MANBECK, JR.

Attesting Officer

Commissioner of Patents and Trademarks